United States Patent
Ryu et al.

Patent Number: 5,672,726
Date of Patent: Sep. 30, 1997

[54] METHOD FOR SEPARATING AND PURIFYING α-LINOLENIC ACID FROM PERILLA OIL

[75] Inventors: Su-Noh Ryu, Chungchongnam-do; Jung-Il Lee, Seoul; Bo-Young Jeong, Tongyoeng; Han-Sun Hur, Suwon, all of Rep. of Korea

[73] Assignee: Republic of Korea Represented by Rural Development Administration, Suwon, Rep. of Korea

[21] Appl. No.: 512,829

[22] Filed: Aug. 9, 1995

[30] Foreign Application Priority Data

Dec. 9, 1994 [KR] Rep. of Korea ............... 1994-33544

[51] Int. Cl.[6] ............................................... C07C 1/60
[52] U.S. Cl. ................... 554/20; 554/8; 423/335; 556/110; 556/400
[58] Field of Search ................. 554/8, 20; 556/110, 556/400; 423/335

[56] References Cited

FOREIGN PATENT DOCUMENTS 1-207257  8/1989  Japan.

*Primary Examiner*—Deborah D. Carr
*Attorney, Agent, or Firm*—Foley & Lardner

[57] ABSTRACT

Disclosed herein is a method for separating and purifying α-linolenic acid (ALA) from ALA-containing fatty acid mixtures by using a column chromatography, comprises the steps of:

packing a column with silver nitrate(AgNO$_3$)-impregnated silica gel as a stationary phase;

passing the ALA-containing fatty acid mixtures through the column to adsorb the fatty acids to the stationary phase in the form of Ag$^+$-complexes;

eluting the fatty acids with acetone-hexane mixtures; and collecting the fractions containing ALA having a purity of more than 95%.

5 Claims, 3 Drawing Sheets

METHOD FOR SEPARATING AND PURIFYING α-LINOLENIC ACID FROM PERILLA OIL

BACKGROUND OF THE INVENTION

1. Fields of the Invention

The present invention is generally related to a method for separating and purifying α-linolenic acid from perilla oil, and more particularly is related to a method for separating and purifying α-linolenic acid from perilla oil by silver nitrate-impregnated silica gel column chromatography using acetone-hexane solvents as an eluent.

2. Prior Art

α-Linolenic acid(18:3n-3, hereinafter abbreviated as "ALA") is one of n-3 series unsaturated acids such as eicosapentaenoic acid(20:5n-3, EPA) and docosahexaenoic acid(22:6n-3, DHA) and its various physiological activities, for example, anti-cancer action, thrombosis-suppressing action, anti-hypertension, anti-allergy action, memory-increasing action and so on have been reported.

ALA is plentifully contained in perilla oil and may be separated therefrom by conventional hydrolysis. But, the hydrolysis of perilla oil gives ALA in admixture with other unsaturated acids, such as linoleic acid(18:2n-6) and oleic acid(18:1n-9). Accordingly, the ALA product of conventional hydrolysis of perilla oil can not be employed for physiological test, which requires 90% or more purity. Thus, ALA obtained by conventional hydrolysis is of no practical use, and a new method for producing ALA having 90% or more purity, or preferably 95% or more purity has been needed.

Recently, Japanese Patent 1-207257A discloses a method for separating and purifying ALA from a mixture of ALA, 18:2n-6 and 18:1n-9, which comprises using a reverse phase partition chromatography. The chromatography employs octadecyl group-coupled silica gel or styrene-divinylbenzene copolymer as a carrier, and aqueous N,N-dimethyl formamide solution, aqueous methanol solution or dimethyl sulfoxide as an eluent. By this method, ALA having 90% or more purity can be obtained.

Under these circumstances, the present inventors have conducted extensive studies to provide a purification method which can produce ALA having 95% or more purity. As a result, we got a conception that certain fatty acid can be separated from the fatty acid mixtures obtained from perilla oil by a conventional hydrolysis by using a difference in the polarities of the fatty acids, said difference of the polarity being resulted from the different numbers of double bond contained in each fatty acid.

In detail, in a purification method by column chromatography, wherein silver nitrate($AgNO_3$)-impregnated silica gel is used as a stationary phase, silver ion($Ag^+$) forms reversibly polar complexes by attacking the double bonds of fatty acids. Therefore, by controlling the polarity of eluent solvent, which is applied continuously to the column, it is possible to specifically separate ALA from the fatty acid mixture.

SUMMARY OF THE INVENTION

Thus, an object of the invention is to provide a method for separating and purifying ALA from ALA-containing fatty acid mixtures.

This object can be achieved by the method according to the present invention, which comprise the steps of:

packing a column with silver nitrate($AgNO_3$)-impregnated silica gel as a stationary phase;

passing the ALA-containing fatty acid mixtures through the column to adsorb the fatty acids to the stationary phase in the form of $Ag^+$-complexes;

eluting the fatty acids with acetone-hexane mixtures; and collecting the fractions containing ALA having a purity of more than 95%.

DETAILED DESCRIPTION OF THE INVENTION

Figure 1:
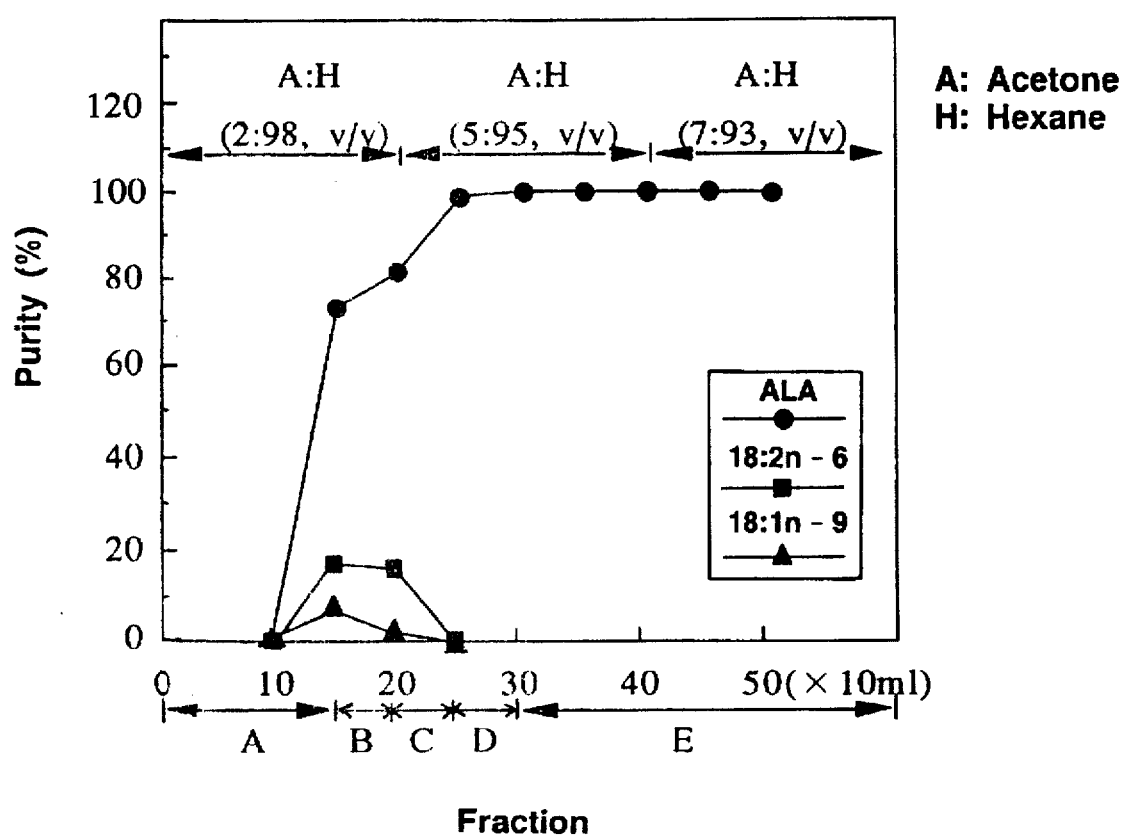
FIG. 1 shows the result of GLC analysis of each fraction separated from ALA-containing fatty acid mixture according to Example 1 of the present invention.

The term "ALA-containing fatty acid mixture" used in the present invention means hydrolysates of perilla oil, or concentrates thereof obtained by a low-temperature crystallization, or any acid mixtures having the equivalent composition as those in Table 1 or Table 2 regardless of their sources. The following Table 1 shows that a typical composition of hydrolysates of perilla oil: it contains 63.1% of ALA, 14.1% of 18:1n-9, and 14.0% of 18:2n-6, and 9.0% is occupied by other acids such as 16:0(palmitic acid) and 18:0(stearic acid). Further, Table 2 shows that a concentrate obtained by crystallizing said hydrolysate at a low temperature contains about 76% of ALA. Thus, a low-temperature crystallization can increase a separation efficiency of ALA.

TABLE 1

| Fatty acids contained in a hydrolysate of perilla oil | |
|---|---|
| Fatty acid | content (%) |
| 16:0 | 6.22 |
| 18:0 | 1.68 |
| 18:1n-9 | 14.1 |
| 18:1n-7*Note | 0.90 |
| 18:2n-6 | 14.0 |
| 18:3n-3 | 63.1 |

*Note: 18:1n-7 is a oleic acid having one double bond at the 7-position.

TABLE 2

| Fatty acids contained in a concentrate obtained by low-temperature crystallization of the hydrolysate | |
|---|---|
| Fatty acid | content (%) |
| 16:0 | 0.31 |
| 18:1n-9 | 6.73 |
| 18:1n-7 | 1.05 |
| 18:2n-6 | 16.1 |
| 18:3n-3 | 75.8 |

According to the present invention, a column chromatography is employed to separate ALA from the ALA-containing fatty acid mixture, wherein silver nitrate-impregnated silica gel is employed as a stationary phase. Silver nitrate-impregnated silica gel can be prepared by common methods, for example by impregnating about 10 g of silver nitrate($AgNO_3$) per 100 g of silica gel(70 to 230 mesh).

The eluents used in the chromatography according to the present invention will now be described in detail.

Unsaturated fatty acids contained in the ALA-containing fatty acid mixture, namely, ALA, 18:2n-6 and 18:1n-9 have the different numbers of double bonds, while all of them have 18 carbon atoms. These differences in the number of double bond cause differences in polarities of these fatty acids in order of 18:1n-9<18:2n-6<18:3n-3(ALA). When the ALA-containing fatty acid mixture is passed through the column packed with silver nitrate-impregnated silica gel, the fatty acids contained in the mixture are adsorbed to the stationary phase, forming polar complexes with silver ion ($Ag^+$) and can be selectively eluted in order of their polarities, from low to high polarity by changing the polarities of the eluents. Thus, for the present invention, as an eluent, acetone-hexane mixtures are employed and their polarities can be regulated by changing the content of acetone. That is to say, by increasing the polarity of eluent, i.e. by increasing the content of acetone in the eluent, the fatty acids can be eluted in order of 18:1n-9, 18:2n-6 and next ALA. The acetone content of the eluent, an acetone-hexane mixture changes from about 2% by volume to about 7% by volume. Specifically, three acetone-hexane mixtures are employed, wherein the acetone content is about 2%, 5% and 7% by volume; respectively, in that order.

The ALA-containing fatty acid mixture is passed through the column in an amount of 2 to 3 g per 100 g of stationary phase. Then, three eluents are passed through the column in an amount of 200 ml for each, at the flow rate of 1 to 2 ml/min.

As described above, the present invention, by utilizing the difference in a polarities of the fatty acids, provides a new method capable of highly purifying ALA from a mixture containing ALA and other fatty acids having the same carbon numbers as ALA has. Moreover, since the solvents employed as an eluent have relatively low polarity, silver ion($Ag^+$) is scarcely eluted, and thereby silver nitrate-impregnated silica gel can be used semipermanently and cost for purification can be reduced greatly.

PREFERRED EMBODIMENT OF THE INVENTION

The present invention will be described in more detail by way of the following non-limiting Examples.

EXAMPLE 1

Silver nitrate-impregnated silica gel to be employed as a stationary phase, was prepared as follows.

10 g of silver nitrate($AgNO_3$) was dissolved in 300 ml of ethanol and then 100 g of silica gel(70 to 230 mesh) was dispersed therein. After mixing them for 10 minutes, ethanol was removed completely, and the silica gel was activated by heating to 120° C. for 2 hours and then stood in a desiccator for 30 minutes. Thus obtained silver nitrate-impregnated silica gel was dispersed in acetone-hexane(2:98, v/v) and then was filled in a glass column(2.5 cm, i.d.×30 cm).

The ALA-containing fatty acid mixture was employed a hydrolysate of perilla oil having a composition shown in Table 1.

2.5 g of hydrolysate of perilla oil, where the fatty acids were present in the form of methyl ester derivatives, was passed through the column, and as a eluent, three acetone-hexane mixtures(i.e. acetone: hexane=2:98, 5:95 and 7:93, v/v, respectively) were consecutively passed through the column in that order, each in an amount of 200 ml, at the flow rate of 1–2 ml/min. And, the eluates were collected using a 10 ml of fraction collector. The collected fractions were washed with 1% of aqueous NaCl solution and then with distilled water so as to remove the impurities. Then, the purity of the obtained ALA was measured by gas-liquid chromatography(GLC), and the ALA fractions having similar purities were collected. Again, in order to measure the purity and the weight of ALA, these fractions were applied to gas-liquid chromatography, wherein an inner standard sample was 23:0 methyl ester.

The condition in the GLC analysis is as follows:

GLC : Shimadzu GC 14A

Column: Supelcowax-10 fused silica wall coated open-tubular capillary column(0.50 mm, i.d.×25 m)

Column temperature: 180°–220 ° C.

Injector temperature: 250° C.

Detector temperature: 250° C.

Split ratio: 1:50

Carrier gas: He (1.0 kg/$cm^2$)

Integrator : Shimadzu CR-5

The composition of each fraction was shown in FIG. 1 and the purity of ALA of fatty acids contained in each fraction was 79.4% for fraction B; 88.2% for fraction C; 99.6% for fraction D; and 99.9% for fraction E. Further, the recovery factor of ALA was 90.2% for fractions B+C+D+E; 52.8% for fractions C+D+E; 36.8% for fractions D+E; and 16.4% for fraction E.

EXAMPLE 2

The purification of ALA was carried out by the same procedure as described in Example 1, except that a concentrate obtained by crystallizing the hydrolysate at a low temperature was employed as an ALA-containing fatty acid mixture.

A concentrate were prepared by a low-temperature crystallization. In more detail, a hydrolysate of perilla oil was dissolved in 7 times volume of 98% of aqueous acetone solution, and then the solution were freezed at −80° C. for 1 hour. Then, the solution was filtered through Büchner funnel to give a concentrate having the composition shown in Table 2. The purification of ALA was carried out by the same procedure as described in Example 1.

Figure 2:
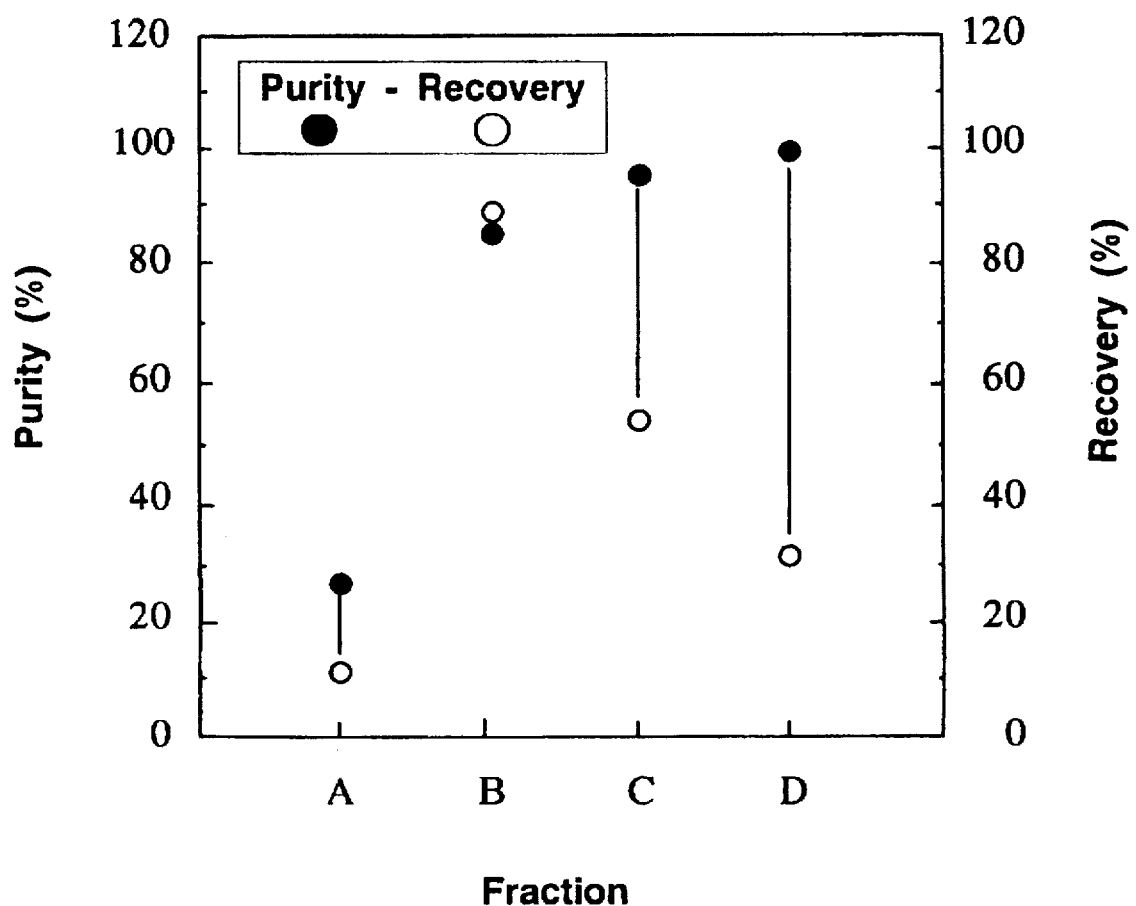
FIG. 2 shows the result of GLC analysis of each fraction separated from ALA-containing fatty acid mixture according to Example 2 of the present invention.
Figure 3:
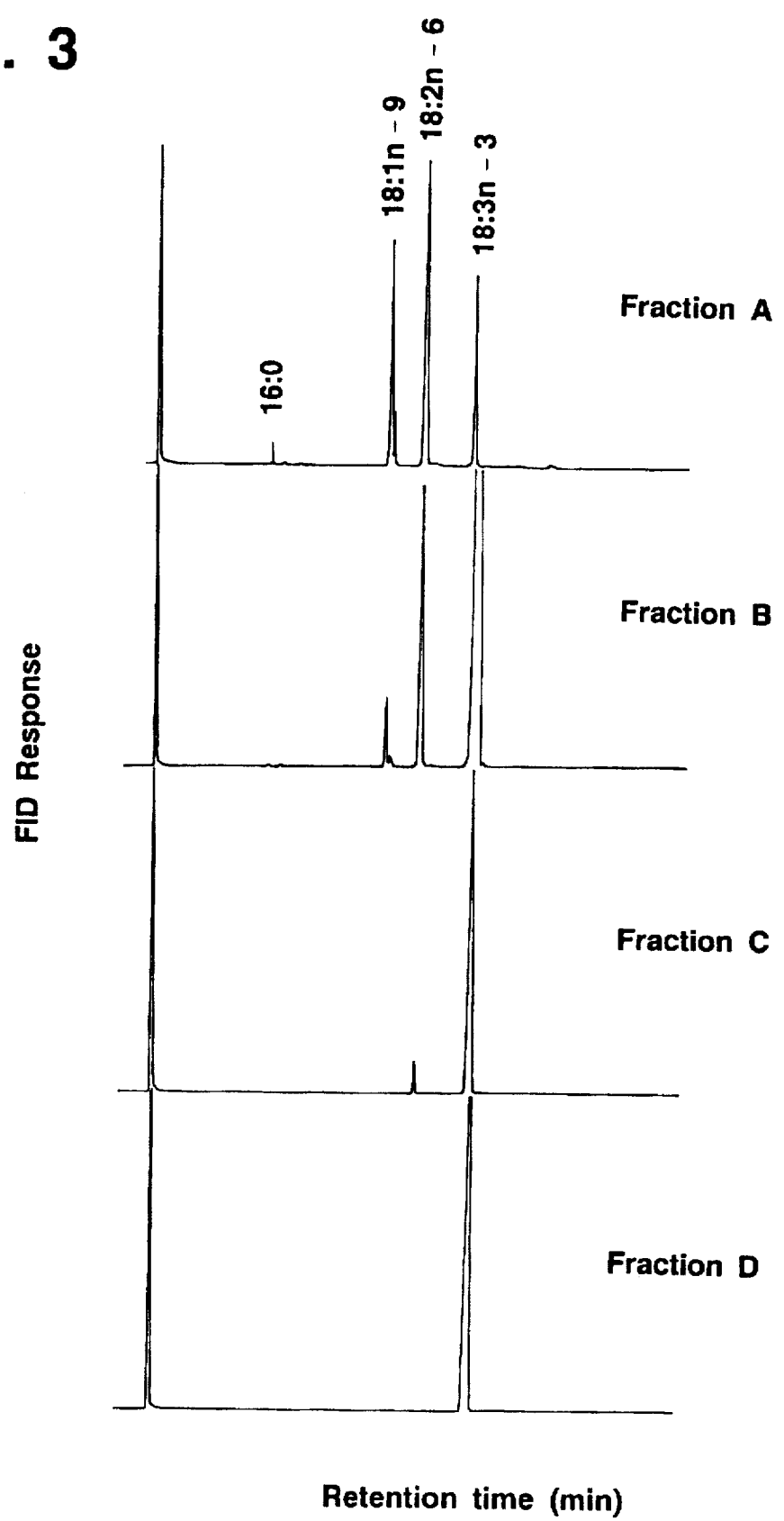
FIG. 3 is GLC Chromatogram of each fraction separated from ALA-containing fatty acid mixture according to Example 2 of the present invention.

The composition of each fraction was shown in FIG. 2 and the purity of ALA of fatty acids contained in each fraction was 85.5% for fraction B; 95.4% for fraction C; and 99.9% for fraction D. Further, the recovery factor of ALA was 90.0% for fractions B+C+D; 54.4% for fractions C+D; and 31.5% for fraction

EXAMPLE 3

The purification of ALA was carried out by the same procedure as described in Example 2, except that silver nitrate-impregnated silica gel column used in Example 1 was used as a column for the purification.

The purity of ALA of fatty acids contained in each fraction was 85.6% for fraction B; 95.4% for fraction C; and 99.8% for fraction D. Further, the recovery factor of ALA was 89.9% for the fractions B+C+D; 54.5% for fractions C+D; and 31.3% for fraction D.

EXAMPLE 4

The purification of ALA was carried out by the same procedure as described in Example 2, except that silver nitrate-impregnated silica gel column used in Example 3 was used as a column for the purification.

The purity of ALA of fatty acids contained in each fraction was 85.4% for fraction B; 95.2% for fraction C; and 99.9% for fraction D. Further, the recovery factor of ALA was 90.2% for fractions B+C+D; 56.1% for fractions C+D; and 31.3% for fraction D.

What is claimed is:

1. A method for separating and purifying α-linolenic acid (ALA) from ALA-containing fatty acid mixtures by using a column chromatography, comprises the steps of:

packing a column with silver nitrate($AgNO_3$)-impregnated silica gel as a stationary phase;

passing the ALA-containing fatty acid mixtures through the column to adsorb the fatty acids to the stationary phase in the form of $Ag^+$-complexes;

eluting the fatty acids with acetone-hexane mixtures; and collecting the fractions containing ALA having a purity of more than 95%.

2. The method as claimed in claim 1, wherein said ALA-containing fatty acid mixtures are hydrolysates of perilla oil or concentrates thereof obtained by a low-temperature crystallization.

3. The method as claimed in claim 1, wherein said ALA-containing fatty acid mixtures are passed through the column in an amount of 2 to 3 g per 100 g of the stationary phase.

4. The method as claimed in claim 1, wherein said silver nitrate-impregnated silica gel is prepared by impregnating about 10 g of silver nitrate($AgNO_3$) per 100 g of 70–230 mesh silica gel.

5. The method as claimed in claim 1, wherein the fatty acids are eluted by passing, as eluents, three acetone-hexane mixtures wherein the volume ratio of acetone:hexane are about 2:98, about 5:95, and about 7:93, respectively, in that order, through the column.

* * * * *